United States Patent [19]

Grieco

[11] Patent Number: 4,699,996
[45] Date of Patent: Oct. 13, 1987

[54] 12,16-DIFLUOROPROSTAGLANDIN $F_2 \alpha$ COMPOUNDS

[76] Inventor: Paul A. Grieco, 1480 Southdowns Dr., Bloomington, Ind. 47401

[21] Appl. No.: 829,864

[22] Filed: Feb. 18, 1986

Related U.S. Application Data

[63] Continuation of Ser. No. 530,097, Sep. 7, 1983, abandoned.

[51] Int. Cl.$^4$ .......................................... C07C 177/00
[52] U.S. Cl. .................................... 560/121; 562/503
[58] Field of Search ........................ 560/121; 562/503

[56] References Cited

U.S. PATENT DOCUMENTS 4,284,794  8/1981  Grieco ................................ 560/121

OTHER PUBLICATIONS

Grieco, J. Med. Chem. 23, 1073 (1980), (Table 1).

Primary Examiner—Robert Gerstl
Attorney, Agent, or Firm—Allegretti, Newitt, Witcoff & McAndrews, Ltd.

[57] ABSTRACT

This invention relates to novel 12,16-difluoroprostaglandin $F_{2\alpha}$ compounds having leuteolytic activity.

6 Claims, No Drawings

12,16-DIFLUOROPROSTAGLANDIN $F_2\alpha$ COMPOUNDS

This application is a continuation application of U.S. application Ser. No. 530,097, filed Sept. 7, 1983, now abandoned.

BACKGROUND OF THE INVENTION (a) Field of the Invention

This invention relates to 12,16-difluoroprostaglandin $F_2$, its salts and its esters, and epimers thereof, which exhibit leuteolytic activity and are useful as mensturual regulators.

(b) Information Disclosure

Grieco et al, J. Med. Chem, 23, 1072 (1980), describes the synthesis and biological evaluation of the methyl esters of (+)-12-fluoro-, (−)-ent-12-fluoro-, (+)-15-epi-fluoro-, and (−)-ent-15-epi-12-fluoroprostaglandin $F_{2\alpha}$. Those compounds were active in the hamster antifertility assay.

SUMMARY OF THE INVENTION

The invention relates to compounds of the formula

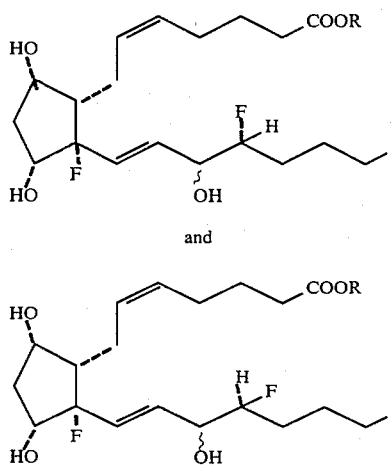

and wherein R is H, alkali metal such as Na or K, and lower alkyl having 1-4 carbon atoms inclusive, such as methyl, ethyl, propyl, isopropyl, butyl and the various isomers thereof. The wavy line indicates the hydroxy bond may be "solid line" giving the "normal" or 15R configuration for $PGF_2$ compounds, or the bond may be "dotted line" giving the "epi" or 15S configuration.

Leuteolytic activity was determined by the interruption of pregnancy test carried out in hamsters essentially according to the method of Giannina. The test is run on female hamsters during the first seven days after mating. The compound to be tested is administered, subcutaneously or intragastrically, at the rate of 50 mg/kg daily for five days and the animals are autopsied on day seven. A dose of compound is rated active if the implanatation rate (total sites ×100/total corporea lutea) is 50% or less. The $ED_{50}$ is the dose which reduces the implanation rate to 50%.

The compounds of the invention are prepared using an appropriate analogous to that described by Grieco et al, *J. Med. Chem.* 23 1072 (1980). The protected bicyclic alcohol (−)-7-fluoro-spiro[bicyclo[2,2,1]hept-5-ene-2,2'-[1,3]dioxolane]-7-methanol is converted to the corresponding protected aldehyde by oxidation with Collins reagent and condensed with dimethyl (R) or (S)-3-fluoro-2-oxoheptylphosphonate in the presence of very strong base such as sodium hydride. The resultant (−)-[1α,4α,7S*(E)]-fluoro-spiro[(bicyclio[2,2,1]-hept-5-ene-2,2'-[1,3]-dioxolan)-7-yl-4-fluoro-1-octen-3-one is reduced to the corresponding protected alcohol, for example with lithium aluminum hydride. The alcohol is deketalized in acidic solution, oxidized to the dihydroxy acid, and converted to the bicyclic lactone using the standard procedure (a) iodolactonization (b) deiodination and (c) tetrahydropyranylation. Elaboration of the C(8) side chain is carried out using the three step sequence (a) reduction with diisobutyl aluminum hydride (b) condensation of the resultant lactol with the witting reagent derived from 5-triphenyl-phosphonovaleric acid and (c) esterification with diazomethane or lower alkanol. Cleavage of the 15-RS tetrahydropyranyl ethers yielded the 15R and the 15S (epi) ester compounds of the invention, which are separated chromatographically. The corresponding acids are prepared by saponification of the esters followed by acidification. Salts are prepared by reaction of the acid with the appropriate metal hydroxide or carbonate, or directly from the ester during saponification. Higher esters can be prepared from lower esters by alcoholysis.

The compounds of the invention can be administered in number of dosage forms, for example in oral unit dosage form as tablets, capsules, pills, powders or granules. They also may be administered rectally or vaginally as suppositories, intraperitoneally, subcutaneously, or intramuscularly in solution using vehicles known to the pharmaceutical art.

An effective but non-toxic quantity of the compound is employed in treatment. The dosage regimen for the regularization of menses by the compounds of this invention is selected in accordance with variety of factors including the type, age, weight, and medical condition of the mammal, the route of administration and the particular compound employed. In general, the dosage utilized ranges from 1-5 mg/kg. of body weight.

The invention will appear more fully from the Examples which follow. These Examples are given by way of illustration only and are not to be construed as limiting the invention either in spirit or in scope, as many modifications both in materials and methods will be apparent from this disclosure to those skilled in the art.

EXAMPLE I

A.

(−)-[1α,4α,7S*(E)]-7-fluorospiro[bicyclo[2,2,1]hept-5-ene-2,2'-[1,3]dioxolane]-7-yl-4(R)-fluoro-1-octen-3-one To solution of Collins reagent prepared from 825 mg (8.25 mmole) of $CrO_3$, 1.34 ml of anhydrous pyridine, 4.3 g of Celite 545 and 20 ml of $CH_2Cl_2$, was added 110 mg (0.55 mmole) of D(−)-7-fluorospiro[bicyclo[2,2,1-]hept-5-ene-2'2'-[1,3]dioxolane]-7-methanol in 2 ml of $CH_2Cl_2$ at 0° C. The reaction was stirred mechanically at 0° C. for 15 min, followed by addition of 4.3 g of $NaHSO_4{}^{19}$ $H_2O$. The reaction was stirred for an additional 10 min. The mixture was filtered through a pad of $MgSO_4$. The solvent was removed under reduced pressure providing the corresponding aldehyde, which was used immediately in the next reaction.

To stirred suspension of 23.2 mg (0.55 mmole) of 56.8% NaH mineral oil dispersion in 6 ml of THF, was added 135 mg (0.56 mmole) of dimethyl [(R)-3-fluoro-2- oxoheptyl]phosphonate in 25 ml of THF. The reaction was stirred at room temperature for 45 min. A solution of the above aldehyde in 2.5 ml of THF was added to the ice-cooled phosphonate anion solution and the mixture was stirred at 0° C. for 30 min. Water was added to quench the reaction. After removal of the solvent under reduced pressure, the residue was dissolved in ether and was washed with brine. The organic layer was dried (MgSO$_4$) and filtered. The solvent was removed under reduced pressure. The crude product was chromatographed on 8 g of silica gel. Elution with hexane-ether (5:1) provided 85 mg (49.5%) of the title enone, $[\alpha]_D^{26} -30°$ (C 3.1, CHCl$_3$).

B.
[1α,4α,7S*(E)]-7-fluorospiro[bicyclo[2,2,1]hept-5-ene-2,2'-4(R)-fluoro-3-hydroxy-1-octenol To solution of 360 mg (1.15 mmole) of the enone from the previous example in 10 ml of MeOH containing 409 mg (1.15 mmole) of CeCl$_3$ H$_2$O was added 44 mg (1.15 mmole) of NaBH$_4$ at 0° C. The reaction mixture was stirred at 0° C. for 10 min. Ammonium chloride solution was added to quench the reaction. After removal of the solvent, water was added to dissolve the residue. The mixture was extracted with EtOAc (X3). The organic layers were washed with brine, dried (MgSO$_4$) and filtered. The solvent was removed under reduced pressure. The crude product was chromatographed on 8 g of silica gel. Elution with hexane-ether (2:1) provided 357 mg (98.5%) of hydroxy ketal which was used directly in the next reaction.

A solution of 357 mg (1.14 mmole) of the above ketal in 9 ml of THF and 3 ml of 10% HCl solution was stirred at room temperature for 14 h. After removal of the solvent under reduced pressure, the residue was diluted with water, and extracted with EtOAc (x3). The combined organic layers were washed with NaHCO$_3$ solution and brine, then dried (MgSO4) and filtered. The solvent was removed under reduced pressure. The crude product was chromatographed on 70 g of silica gel. Elution with hexane-ether (2:1) provided 255 mg (83%; 92% based on recovery of starting material) of the title ketone and 35 mg (9.8%) of recovered ketal.

C.
3,3aα,4R*5β6aα-Hexahydro-5-4-fluoro-4-oxy[4-(R)-fluoro-1-(E)-octenyl]-2H-cyclopenta[b]furan-2-one To solution of 255 mg (0.94 mmole) of the ketone from the previous example in 5.3 ml of MeOH and 4.6 ml of H$_2$O, was added 1.12 ml of 10% NaOH and 0.48 ml of 30% H$_2$O$_2$ solution at 0° C. The reaction mixture was stirred at 0° C. for 4 h and at room temperature for 10 h. After cooling Na$_2$S$_2$O$_5$ solution was added to quench the reaction. This mixture was acidified with 10% HCl solution to pH 5 and was extracted with EtOAc (10 ml×8). The combined organic layers were washed with small amounts of brine (x3), dried (MgSO$_4$) and filtered. The solvent was removed under reduced pressure to provide 281 mg (98%) of the crude dihydroxy acid which was used directly in the next reaction.

Dihydroxy acid (281 mg, 0.92 mmole) was dissolved in 2 ml of water containing 40 mg (1.0 mmole) of NaOH at 0° C. The cooled solution was neutralized to pH ca. 7.0 with the injection of CO$_2$ gas, and treated with solution of 1.68 g (10.12 mmole) of KI and 0.85 g (3.38 mmole) of I$_2$ in 2 ml of water. The resultant black solution was stirred at 0-5° C. for 62 h. Na$_2$S$_2$O$_3$ solution was added to decolorize the solution. The solution was extracted with EtOAc (x3). The combined organic layers were washed with brine, dried (MgSO$_4$) and filtered. The solvent was removed under reduced pressure. The crude product was chromatographed on 8 g of silica gel. Elution with benzene-THF (10:1) provided 295 mg (74%) of pure iodolactone.

To solution of 295 mg (0.69 mmole) of the above iodolactone in 10 ml of anhydrous benzene, was added 0.60 g (2.07 mmole) of nBu$_3$SnH and 10 mg of AzBN. The mixture was heated at 65° C. for 3 h. After removal of the solvent under reduced pressure, the residue was allowed to stand on 70 g of silica gel for 2 h. Elution with Et$_2$O-EtOAc (10:1) provided 153 mg (73%) of the title lactone, mp 121°-122° C.

D.
3,3aα,4R*,5β,6aα)-Hexahydro-5-(tetrahydro-2H-pyran-2-yl)oxy[-4-fluoro-4-[3]tetrahydro-2H-pyranyl-2-yl)-4(R)-fluoro-oxy]-1(E)-octenyl]-2H-cyclopenta[b]furan-2-one A solution of 143 mg (0.47 mmole) of the diol from the previous example in 6 ml of CH$_2$Cl$_2$ containing 119 mg (1.61 mmole) of dihydropyran and 5 mg of PPTS was stirred at room temperature for 4 h. The reaction mixture was diluted with Et$_2$O (~30 ml) and washed with NaHCO$_3$ solution and brine, then dried (MgSO$_4$) and filtered. The solvent was removed under reduced pressure. The residue was chromatographed on 8 g of silica gel. Elution with hexane-Et$_2$O (1:2) provided 210 mg (94.5%) of the title bis-THP ether lactone.

E. 12,16(R)-DifluoroPGF$_{2\alpha}$Methyl Ester BisTHP Ether

To solution 210 mg (0.44 mmole) of the bis THP-ether lactone from the previous example in 5 ml of toluene, was added 1.33 ml of 1M iBu$_2$AlH in hexane at −78° C. under nitrogen. The reaction mixture was stirred at −78° C. for 1 h and −60° C. for an additional hour. Methanol was carefully added to quench the reaction at −60° C. The reaction mixture was diluted with 30 ml of EtOAc and warmed to room temperature followed by the addition of water. After stirring for 1 h, the organic layer was separated. The water layer was treated with NaHSO$_4$ solution to destroy the gelatinous precipitate, and was extracted with EtOAC (x2). The combined organic layers were washed with brine, dried (MgSO$_4$) and filtered. The solvent was removed under reduced pressure. The crude oil was chromatographed on 8 g of silica gel. Elution with hexane-ether (1:2) provided 204 mg (97%) of pure lactol which was used directly in the next reaction.

A suspension of 188 mg (4.44 mmole) of 56.8% NaH mineral oil dispersion in 1.9 ml of freshly distilled DMSO was stirred st 50°-55° C. for 2.5 h under N$_2$. After cooling to room temperature, 985 mg (2.22 mmole) of 4-carboxybutyltriphenylphosphonium bromide (dried at 100° C./0.02 mm Hg prior to use) in 2.3 ml of DMSO was added. After 30 min to the dark red ylide solution was added 204 mg (0.43 mmole) of the above lactol in 1.9 ml of DMSO. The reaction mixture was stirred at room temperature for 1 h. H$_2$O was carefully added to quench the reaction, and additional water (~20 ml) was added. The solution was acidified with NaHSO$_4$ solution to pH ~4 and was extracted with EtOAc (20 ml×3). The combined organic layers were washed with brine, dried (MgSO$_4$) and filtered. The solvent was removed under reduced pressure. The crude acid was treated with etheral diazomethane. After removal of the solvent under reduced pressure, the crude oil was chromatographed on 8 g of silica gel. Elution with hexane-ether (2:1) provided 204 mg (83%) of the title bis THP-ether methyl ester.

F. (+)-12,16(R)-DifluoroPGF$_{2\alpha}$Methyl Ester

A solution of 204 mg (0.36 mmole) of the bis THP-ether methyl ester from the previous example in 5 ml of EtOH containing 10 mg of PPTS was stirred at 60° C. for 9 h. After addition of solid NaHCO$_3$ the solvent was removed under reduced pressure. Water was added to dissolve the residue, and the mixture was extracted with EtOAc (x2). The combined organic layers were washed with brine, dried (MgSO$_4$) and filtered. The solvent was removed under reduced pressure. The residue was chromatographed on 8 g of silica gel. Elution with benzene-ether (1:10) provided 108 mg of crude product.

Recrystallization from hexane-ether gave 29 mg of product directly. The residual 79 mg was purified by Pre TLC (EM Reagents Cat. No. 5766, precoated TLC Plates, silica gel 60 F$_{254}$, 2 mm thickness, 20 cm×20 cm), to obtain an additional 37 mg of title compound, mp 113.5° C., $(\alpha)_D^{29}$ +32.5° (C2.3, CHCl$_3$).

G. (−)-15-epi-12,16(R)-DifluoroPGF$_{2\alpha}$Methyl Ester

From the thin layer chromatographic purification described in the previous example, there was obtained 7.2 mg of the title compound as an oil $(\alpha)_D^{29}$ −1.7° (C=0.72, CHCl$_3$).

EXAMPLE 2

A. (−)-[1α,4α,7S*(E)]-7-Fluorospiro[bicyclo[2,2,1]hept-5-ene-2,2'-[1,3]dioxolan]7-yl-4(S)-fluoro-1-octen-3-one To solution of Collins reagent prepared from 3.15 mg (31.5 mmole) of CrO$_3$, 5.1 ml of anhydrous pyridine, 16.4 g of Celite 545 and 80 ml of CH$_2$Cl$_2$, was added 420 mg (2.1 mmole) of (−)-7-fluorospiro [bicyclo[2,2,1-]hept-5-ene-2'2'-[1,3]dioxolane]-7-methanol 2 in 8ml of CH$_2$Cl$_2$ at 0° C. The reaction was stirred mechanically at 0° C. for 30 min, followed by addition of 16.6 g of NaHSO$_4$$^{19}$ H$_2$O. The reaction was stirred for an additional 10 min. The mixture was filtered through a pad of MgSO$_4$. The solvent was removed under reduced pressure providing the desired aldehyde, which was used immediately in the next reation.

To stirred suspension of 89 mg (2.1 mmole) of 56.8% NaH mineral oil dispersion in 23 ml of THF, was added 532 mg (2.2 mmole) of dimethyl [(S)-3-fluoro-2-oxoheptyl] phosphonate in 10 ml of THF. The reaction was stirred at room temperature for 45 min. A solution of the above aldehyde in 10 ml of THF was added to the ice-cooled phosphonate anion solution and the mixture was stirred at 0° C. for 30 min. Water was added to quench the reaction. After removal of the solvent under reduced pressure, the residue was dissolved in ether and was washed with brine. The organic layer was dried (MgSO$_4$) and filtered. The solvent was removed under reduced pressure. The crude product was chromatographed on 8 g of silica gel. Elution with hexane-ether (5:1) provided 321 mg (49.0%) of the title enone, $[\alpha]_D^{23}$ −98.5° (C=4.0, CHCl$_3$).

B. [1α,4α,7S*(E)-7-Fluorospiro]bicyclo[2,2,1]hept-5-ene-2,2'-4(S)-fluoro-3-hydroxy-1-octenol To solution of 60 mg (0.192 mmole) of the enone from the previous example in 2 ml of MeOH containing 68 mg (0.192 mmole) of CeCl$_3$$^{19}$ H$_2$O was added 7.3 mg (1.15 mmole) of NaBH$_4$ at 0° C. The reaction mixture was stirred at 0° C. for 10 min. Ammonium chloride solution was added to quench the reaction. After removal of the solvent, water was added to dissolve the residue. The mixture was extracted with EtOAc (X3). The organic layers were washed with brine, dried (MgSO$_4$) and filtered. The solvent was removed under reduced pressure. The crude product was chromatographed on 8 g of silica gel. Elution with hexane-ether (2:1) provided 60 mg (99%) of the hydroxy ketal which was used directly in the next reaction.

A solution of 32 mg (0.102 mmole) of the above ketal in 0.75 ml of THF and 0.25 ml of 10% HCl solution was stirred at room temperature for 8 h. After removal of the solvent under reduced pressure, the residue was diluted with water, and extracted with EtOAc (x3). The combined organic layers were washed with NaHCO$_3$ solution and brine, then dried (MgSO$_4$) and filtered. The solvent was removed under reduced pressure. The crude product was chromatographed on 70 g of silica gel. Elution with hexane-ether (2:1) provided 25 mg of the title ketone.

C. 3,3aα,4R*5α,6aα[-Hexahydro-5-4-fluoro-4-[oxy]-4(S)-fluoro-1-(E)-octenyl]-2H-cyclopenta[b]furan-2-one To solution of 274 mg (1.01 mmole) of ketone prepared as in the previous example in 5.7 ml of MeOH and 4.9 ml of H$_2$O, was added 1.20 ml of 10% NaOH and 0.52 ml of 30% H$_2$O$_2$ solution at 0° C. The reaction mixture was stirred at 0° C. for 5 h and at room temperature for 13 h. After cooling Na$_2$S$_2$O$_5$ solution was added to quench the reaction. This mixture was acidified with 10% HCl solution to pH 5 and was extracted with EtOAc (10 ml×8). The combined organic layers were washed with small amounts of brine (x3), dried (MgSO$_4$) and filtered. The solvent was removed under reduced pressure to provide 279 mg (90%) of the crude dihydroxy acid which was used directly in the next reaction.

Dihydroxy acid (279 mg, 0.92 mmole) was dissolved in 2 ml of water containing 40 mg (1.0 mmole) of NaOH at 0° C. The cooled solution was neutralized to pH ca. 7.0 with the injection of CO$_2$ gas, and treated with solution of 1.68 g (10.12 mmole) of KI and 0.85 g (3.38 mmole) of I$_2$ in 2 ml of water. The resultant black solution was stirred at 5° C. for 45 h. Na$_2$S$_2$O$_3$ solution was added to decolorize the solution. The solution was extracted with EtOAc (x3). The combined organic layers were washed with brine, dried (MgSO$_4$) and filtered. The solvent was removed under reduced pressure. The crude product was chromatographed on 8 g of silica gel. Elution with benzene-THF (10:1) provided 274 mg (70%) of pure iodolactone.

To solution of 274 mg (0.64 mmole) of the above iodolactone in 10 ml of dry benzene, was added 0.56 g (1.92 mmole) of nBu$_3$SnH and 10 mg of AzBN. The mixture was heated at 60° C. for 6 h. After removal of the solvent under reduced pressure, the residue was allowed to stand on 70 g of silica gel for 2 h. Elution with Et$_2$O-EtOAc (10:1) provided 132 mg of the title lactone.

D. 3,3aα,4R*,5β,6aα)-Hexahydro-5-tetrahydro-2H-pyran-2-yl[oxy]-4-fluoro-4-[3]tetrahydro-2H-pyranyl-2-yl[-1-oxy-4(S)-fluoro-1(E)-octenyl]-2H-cyclopenta[b]furan-2-one A solution of 130 mg (0.43 mmole) of the diol from the previous example in 6 ml of CH$_2$Cl$_2$ containing 0.12 mg (1.29 mmole) of dihydropyran and 5 mg of PPTS was stirred at room temperature for 4 h. The reaction mixture was diluted with NaHCO$_3$ solution washed with Et$_2$O and brine, then dried (MgSO$_4$) and filtered. The solvent was removed under reduced pressure. The residue was chromatographed on 8 g of silica gel. Elution with hexane-Et$_2$O (1:2) provided 187 mg (92.6%) of the title bis-THP ether lactone.

E. 12,16(S)-DifluoroPGF$_{2\alpha}$Methyl Ester BisTHP Ether

To solution 187 mg (0.40 mmole) of bis THP-ether lactone from the previous example in 4.2 ml of toluene, was added 1.2 ml of 1M iBu$_2$AlH in hexane at −78° C. under nitrogen. The reaction mixture was stirred at −78° C. for 1 h and −60° C. for an additional hour. Methanol was carefully added to quench the reaction at −60° C. The reaction mixture was diluted with 30 ml of EtOAc and warmed to room temperature followed by the addition of water. After stirring for 1 h, the organic layer was separated. The water layer was treated with NaHSO$_4$ solution to destroy the gelatinous precipitate, and was extracted with EtOAC (x2). The combined organic layers were washed with brine, dried (MgSO$_4$) and filtered. The solvent was removed under reduced pressure. The crude oil was chromatographed on 8 g of silica gel. Elution with hexane-ether (1:2) provided 169 mg (90%) of pure lactol which was used directly in the next reaction.

A suspension of 169 mg (4.0 mmole) of 56.8% NaH mineral oil dispersion in 1.7 ml of freshly distilled DMSO was stirred st 50°-55° C. for 2.5 h under N$_2$. After cooling to room temperature, 887 mg (2.0 mmole) of 4-carboxybutyltriphenylphosphonium bromide (dried at 100° C. under vacuum prior to use) in 1.7 ml of DMSO was added. After 30 min to the dark red ylide solution was added 169 mg (0.40 mmole) of the above lactol in 1.7 ml of DMSO. The reaction mixture was stirred at room temperature for 30 min. H$_2$O was carefully added to quench the reaction, and additional water (∼20 ml) was added. The solution was acidified with NaHSO$_4$ solution to pH ∼4 and was extracted with EtOAc (20 ml×3). The combined organic layers were washed with brine, dried (MgSO$_4$) and filtered. The solvent was removed under reduced pressure. The crude acid was treated with etheral diazomethane. After removal of the solvent under reduced pressure, the crude oil was chromatographed on 8 g of silica gel. Elution with hexane-ether (2:1) provided 199 mg of the title bis THP-ether methyl ester.

F. (+)-12,16(S)-DifluoroPGF$_{2\alpha}$Methyl Ester

A solution of 199 mg of bis THP-ether methyl esters from the previous example in 5 ml of EtOH containing 10 mg of PPTS was stirred at 50° C. for 16 h. After addition of solid NaHCO$_3$ the solvent was removed under reduced pressure. Water was added to dissolve the residue, and the mixture was extracted with EtOAc (x2). The combined organic layers were washed with brine, dried (MgSO$_4$) and filtered. The solvent was removed under reduced pressure. The 180 mg residue was chromatographed on 8 g of silica gel using benzene-tetrahydrofuran-formic acid 15:15:1, and rechromatographed with benzene-ether 1:1.

The lower portion was rechromatographed using hexane-ether as the elution solvent. Recrystallization of the residue from hexane-ether gave the title compound mp 103°-104° C., $(\alpha)_D^{29}$+10° (C=0.40, CHCl$_3$).

G. (−)-15-epi-12,16(S)-DifluoroPGF$_{2\alpha}$Methyl Ester

The upper portion from the previous example was rechromatographed using hexane-ether as the elution solvent. Evaporation of the solvent gave the title compound as an oil $[\alpha]_D^{29}$−16.6° (C=2.21, CHCl$_3$).

I claim:

1. Compounds of the formula

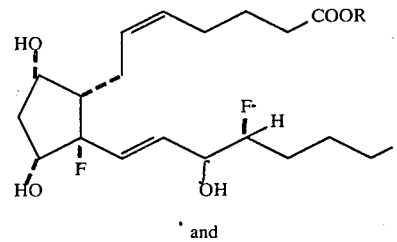

and

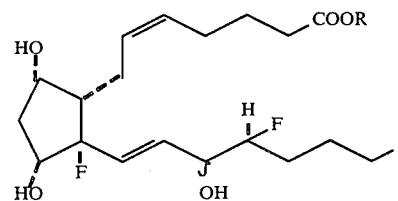

wherein R is H, alkali metal or lower alkyl having 1-4 carbon atoms.

2. Compounds according to claim 1 wherein R is methyl.

3. Methyl (+)-12,16-(R)-difluoroprostaglandin F$_{2\alpha}$, a compound according to claim 2.

4. Methyl (+)-12,16(S)-difluoroprostaglandin F$_{2\alpha}$, a compound according to claim 2.

5. Methyl (−)-15-epi-12,16-(R)-difluoroprostaglandin F$_{2\alpha}$, a compound according to claim 2.

6. Methyl (−)-15-epi-12,16(S)-difluoroprostaglandin F$_{2\alpha}$, a compound according to claim 2.

* * * * *